(12) United States Patent
Peyman

(10) Patent No.: US 7,993,399 B2
(45) Date of Patent: Aug. 9, 2011

(54) EXTERNAL LENS ADAPTED TO CHANGE REFRACTIVE PROPERTIES

(75) Inventor: Gholam A. Peyman, Sun City, AZ (US)

(73) Assignee: Gholam A. Peyman, Sun City, AZ (US)

( * ) Notice: Subject to any disclaimer, the term of this patent is extended or adjusted under 35 U.S.C. 154(b) by 323 days.

(21) Appl. No.: 11/426,224

(22) Filed: Jun. 23, 2006

(65) Prior Publication Data

US 2007/0142909 A1    Jun. 21, 2007

Related U.S. Application Data

(63) Continuation-in-part of application No. 11/259,781, filed on Oct. 27, 2005, now abandoned.

(51) Int. Cl.
*A61F 2/16* (2006.01)

(52) U.S. Cl. ............... 623/6.22; 623/6.19; 623/6.34; 623/6.35

(58) Field of Classification Search .......... 623/6.13, 623/6.22, 6.27, 6.59
See application file for complete search history.

(56) References Cited

U.S. PATENT DOCUMENTS

| | | | |
|---|---|---|---|
| 4,373,218 A * | 2/1983 | Schachar ............. 623/6.13 |
| 4,563,565 A | 1/1986 | Kampfer et al. |
| 4,575,373 A | 3/1986 | Johnson |
| 4,676,790 A | 6/1987 | Kern |
| 4,718,418 A | 1/1988 | L'Esperance, Jr. |
| 4,731,078 A * | 3/1988 | Stoy et al. ............. 623/6.13 |
| 4,787,903 A | 11/1988 | Grendahl |
| 4,816,031 A | 3/1989 | Pfoff |
| 4,840,175 A | 6/1989 | Peyman |
| 4,892,543 A | 1/1990 | Turley |
| 4,976,709 A | 12/1990 | Sand |
| 4,994,058 A | 2/1991 | Raven et al. |
| 5,098,444 A | 3/1992 | Feaster |
| 5,120,121 A | 6/1992 | Rawlings et al. |
| 5,196,027 A | 3/1993 | Thompson |
| 5,201,762 A | 4/1993 | Hauber |
| 5,336,261 A | 8/1994 | Barrett et al. |
| 5,443,506 A | 8/1995 | Garabet |
| 5,476,515 A | 12/1995 | Kelman et al. |
| 5,607,472 A | 3/1997 | Thompson |
| 5,647,865 A | 7/1997 | Swinger |
| 5,722,971 A | 3/1998 | Peyman |
| 5,824,086 A | 10/1998 | Silvestrini |
| 5,876,442 A | 3/1999 | Lipshitz et al. |
| 5,919,185 A | 7/1999 | Peyman |

(Continued)

OTHER PUBLICATIONS

Karin R. Sletten, MD et al.; Experimental Science, "An In Vivo Model of Femtosecond Laser Intrastromal Refractive Surgery", Ophthalmic Surgery and Lasers, Nov.-Dec. 1999, vol. 30, No. 9, pp. 742-749.

(Continued)

*Primary Examiner* — Corrine M McDermott
*Assistant Examiner* — Christopher D Prone
(74) *Attorney, Agent, or Firm* — Wenderoth, Lind & Ponack, L.L.P.

(57) ABSTRACT

A lens system is provided. The lens system includes a lens adapted to be positioned along the main optical axis of the eye and a control unit. The control unit is operable with the lens to alter the focal length of the lens based at least partly upon a condition, such that the lens alters light rays and focuses the rays on the retina of the eye.

22 Claims, 8 Drawing Sheets

U.S. PATENT DOCUMENTS

| | | | |
|---|---|---|---|
| 5,928,283 | A | 7/1999 | Gross et al. |
| 6,066,171 | A | 5/2000 | Lipshitz et al. |
| 6,102,946 | A | 8/2000 | Nigam |
| 6,197,019 | B1 | 3/2001 | Peyman |
| 6,357,875 | B1 | 3/2002 | Herrick |
| 6,358,280 | B1 | 3/2002 | Herrick |
| 6,361,560 | B1 | 3/2002 | Nigam |
| 6,413,276 | B1 | 7/2002 | Werblin |
| 6,450,642 | B1 | 9/2002 | Jethmalani et al. |
| 6,596,026 | B1 | 7/2003 | Gross et al. |
| 6,702,807 | B2 | 3/2004 | Peyman |
| 6,749,632 | B2 | 6/2004 | Sandstedt et al. |
| 6,813,097 | B2 | 11/2004 | Jethmalani et al. |
| 6,824,266 | B2 | 11/2004 | Jethmalani et al. |
| 6,851,804 | B2 | 2/2005 | Jethmalani et al. |
| 6,935,743 | B2 * | 8/2005 | Shadduck ............ 351/160 R |
| 6,947,782 | B2 | 9/2005 | Schulman et al. |
| 7,041,133 | B1 * | 5/2006 | Azar .................. 623/6.22 |
| 2002/0016629 | A1 * | 2/2002 | Sandstedt et al. ........ 623/6.11 |
| 2002/0042004 | A1 | 4/2002 | Sandstedt et al. |
| 2002/0167735 | A1 | 11/2002 | Jethmalani et al. |
| 2002/0169505 | A1 | 11/2002 | Jethmalani et al. |
| 2002/0197584 | A1 * | 12/2002 | Kendir et al. ............ 434/21 |
| 2003/0018383 | A1 * | 1/2003 | Azar .................. 623/6.22 |
| 2003/0048411 | A1 | 3/2003 | Jethmalani et al. |
| 2003/0060878 | A1 * | 3/2003 | Shadduck .............. 623/6.13 |
| 2003/0090013 | A1 | 5/2003 | Jethmalani et al. |
| 2003/0090624 | A1 | 5/2003 | Jethmalani et al. |
| 2003/0093150 | A1 | 5/2003 | Jethmalani et al. |
| 2003/0128336 | A1 | 7/2003 | Jethmalani et al. |
| 2003/0151825 | A1 | 8/2003 | Bielawski et al. |
| 2003/0151831 | A1 | 8/2003 | Sandstedt et al. |
| 2003/0176521 | A1 | 9/2003 | Jethmalani et al. |
| 2005/0099597 | A1 | 5/2005 | Sandstedt et al. |

OTHER PUBLICATIONS

Griffith et al., "Functional Human Corneal Equivalents Constructed from Cell Lines", Science, vol. 286, Dec. 10, 1999, pp. 2169-2172.

Yamauchi et al.; "Cultivation of fibroblast cells on keratin-coated substrata", Polymers for Tissue Engineering, pp. 329-340, VSP 1998.

Ijima et al.; "Formation of spherical multicellular aggregate (spheroid) of animal cells in the pores of polyurethane form as a cell culture substratum and its application to a hybrid artificial liver", Polymers for Tissue Engineering, pp. 273-286, VSP 1998.

Cao et al.; "Comparative study of the use of poly(glycolic acid), calcium alginate and pluronics in the engineering of autologous porcine cartilage", Polymers for Tissue Engineering, pp. 315-327, VSP 1998.

Jose I. Barraquer, MD, "Keratomileusis and keratophakia in the surgical correction of aphakia", pp. 270-289, published before Mar. 21, 2000.

Optics and Photonics News, May 2005, p. 8 "Did you Know?".

Optics Letters, vol. 29, No. 24, Dec. 15, 2004, "Integrated Fluidic Adaptive Zoom Lens".

http://www.primidi.com/2004/12/02.html#a1042. Roland Piquepaille's Technolog Trends, How New Technolgoes Are Modifying Our Way of Life, "Liquid Lenses for Camera Phones," Dec. 2, 2004.

http://www.varioptic.com/en/. Varioptic, The Liquid Lens Company, Dec. 2005.

* cited by examiner

EXTERNAL LENS ADAPTED TO CHANGE REFRACTIVE PROPERTIES

This application is a continuation-in-part of application Ser. No. 11/259,781, now abandoned, entitled "Intraocular Lens Adapted for Accommodation Via Electrical Signals", filed Oct. 27, 2005, the entire contents of which are hereby incorporated by reference.

BACKGROUND

A normal emetropic eye includes a cornea, lens and retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emetropic eye, or a cornea or lens having a refractive power stronger than that of the cornea and lens of an emetropic eye. This stronger refractive power causes the far point to be projected in front of the retina.

Conversely, a hypermetropic or hyperopic eye has an axial length shorter than that of a normal emetropic eye, or a lens or cornea having a refractive power less than that of a lens and cornea of an emetropic eye. This lesser refractive power causes the far point to be focused in back of the retina.

An eye suffering from astigmatism has a defect in the lens or shape of the cornea. Therefore, an astigmatic eye is incapable of sharply focusing images on the retina.

An eye can also suffer from presbyopia. Presbyopia is the inability of the eye to focus sharply on nearby objects, resulting from loss of elasticity of the crystalline lens.

Optical methods are known which involve the placement of lenses in front of the eye, for example, in the form of glasses or contact lenses, to correct vision disorders. A common method of correcting myopia is to place a "minus" or concave lens in front of the eye in order to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. Bifocal lenses can be used to correct presbyopia. The concave, convex or other shaped lenses are typically configured in the form of glasses or contact lenses.

SUMMARY

In one embodiment, a lens system is provided. The lens system includes a lens adapted to be positioned along the main optical axis of the eye and a control unit. The control unit is operable with the lens to alter the focal length of the lens based at least partly upon a condition, such that the lens alters light rays and focuses the rays on the retina of the eye.

In another embodiment, a lens is provided. The lens includes a chamber adapted to house a substance. The lens is adapted to be positioned externally and relative to an eye and coupled to a control unit. The control unit is operable to control the focal length of the lens by influencing the substance, such control of the focal length altering light rays and focusing the light rays on the retina of the eye.

In another embodiment, a control unit is provided. The control unit includes an electronic circuit. The control unit is coupled to a lens, which includes a chamber adapted to house a substance. The lens is adapted to be positioned externally and relative to an eye. The electronic circuit is operable to control the focal length of the lens, such control of the focal length altering light rays and focusing the light rays on the retina of the eye.

Additional features and advantages are described herein, and will be apparent from, the following Detailed Description and the figures.

DETAILED DESCRIPTION

In various embodiments, a lens capable of accommodation in response to electrical signals is provided. The lens can be placed at any suitable location along the optical path of an eye, including but not limited to within the capsular bag, in place of the capsular bag, within the posterior chamber or on, in or behind the cornea. Further, it should be noted that any suitable section of the capsular bag can be removed, including but not limited to an anterior portion or a posterior portion around the main optical axis of the eye. The lens is preferably coupled to a fluidic pumping system which is also coupled to a control system which preferably includes a power source and a signal generation unit.

Figure 1:
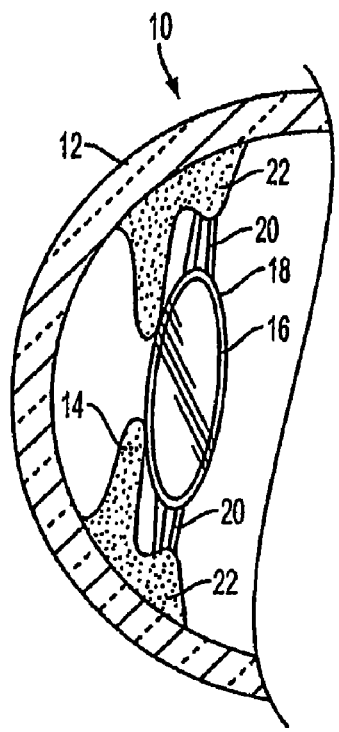
FIG. 1 is a side elevational view in section taken through the center of an eye showing the cornea, pupil, crystalline lens, and capsular bag.

Referring initially to FIG. 1, a normal eye 10 has a cornea 12, an iris 14, and a crystalline lens 16. The crystalline lens 16 is contained within a capsular bag 18 that is supported by zonules 20. The zonules 20, in turn, are connected to the ciliary muscle 22. According to Helmholz's theory of accommodation, upon contraction of the ciliary muscle 22, the tension on the zonules 20 is released. The elasticity of the lens causes the curvature of the lens 16 to increase, thereby providing increased refractive power for near vision. Conversely, during dis-accommodation, the ciliary muscle 22 is relaxed, increasing the tension on the zonules 20 and flattening the lens 16 to provide the proper refractive power for far vision.

Figure 2:
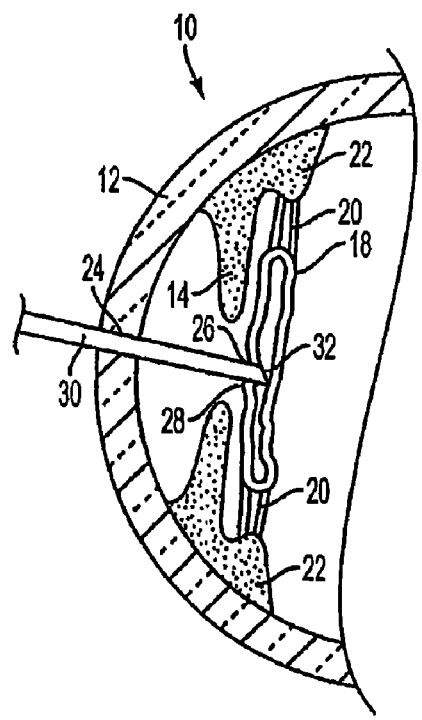
FIG. 2 is a side elevational view in section of the eye shown in FIG. 1 showing the capsular bag after removal of the crystalline lens.

If the electrically accommodating lens is to be positioned within the capsular bag and, thus, replace the crystalline lens, a suitable first step is to remove the existing lens. As illustrated in FIG. 2, the lens is preferably removed using any technique which allows removal of the lens through a relatively small incision, preferably about a 1-2 mm incision. The preferred method is to create a relatively small incision 24 in the cornea 12 and then perform a capsulorhexis to create an opening 26 into the anterior side 28 of the capsular bag 18. An ultrasonic probe 30 is inserted into the capsular bag 18 through the opening 26. The probe's vibrating tip 32 emulsifies the lens 16 into tiny fragments that are suctioned out of the capsular bag by an attachment on the probe tip (not shown). Alternatively, the lensectomy may be performed by laser phacoemulsification or irrigation and aspiration.

Once the crystalline lens 16 has been removed, the capsular bag 18 can be treated to help prevent a phenomenon known as capsular opacification. Capsular opacification is caused by the proliferated growth of the epithelial cells on the lens capsule. This growth can result in the cells covering all or a substantial portion of the front and rear surfaces of the lens capsule, which can cause the lens capsule to become cloudy and thus adversely affect the patient's vision. These cells can be removed by known techniques, such as by scraping away the epithelial cells; however, it is often difficult to remove all of the unwanted cells. Furthermore, after time, the unwanted cells typically grow back, requiring further surgery. To prevent capsular opacification, the capsular bag 18 is preferably treated to eliminate the proliferated growth of epithelial cells, as described below.

Figure 3:
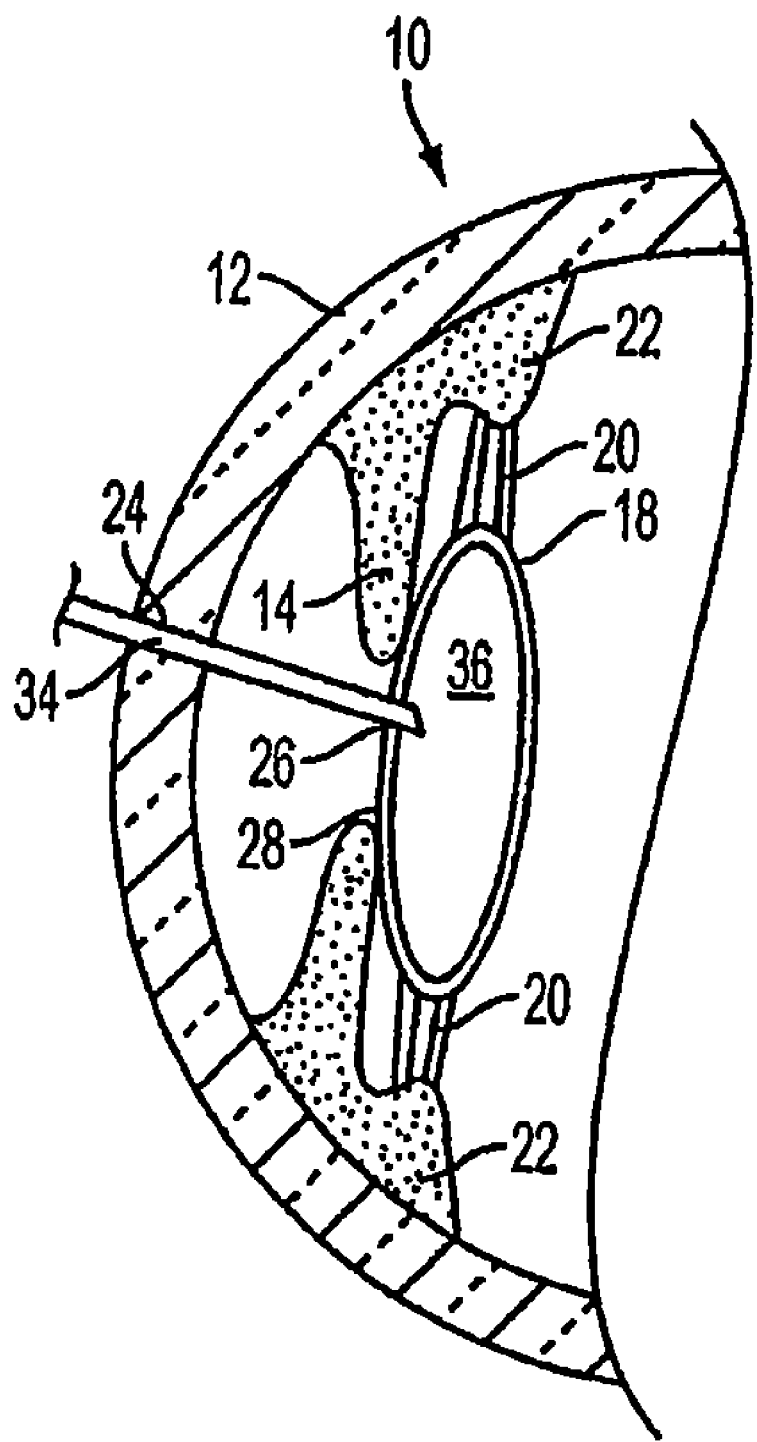
FIG. 3 is a side elevational view in section of the eye shown in FIG. 2 showing the treatment of the interior of the capsular bag with a liquid to prevent capsular opacification.

As seen in FIG. 3, one method of treating the epithelial cells to prevent capsular opacification is to use a cannula 34 to introduce a warm liquid 36 (preferably about <60° C.) into the capsular bag 18, filling the capsular bag 18. The liquid contains a suitable chemical that kills the remaining lens cells in the capsular bag and also cleans the interior of the capsular bag. Suitable chemicals, as well as other suitable methods of treatment that prevent capsular opacification are disclosed in U.S. Pat. No. 6,673,067 to Peyman, which is herein incorporated by reference in its entirety.

Figure 4:
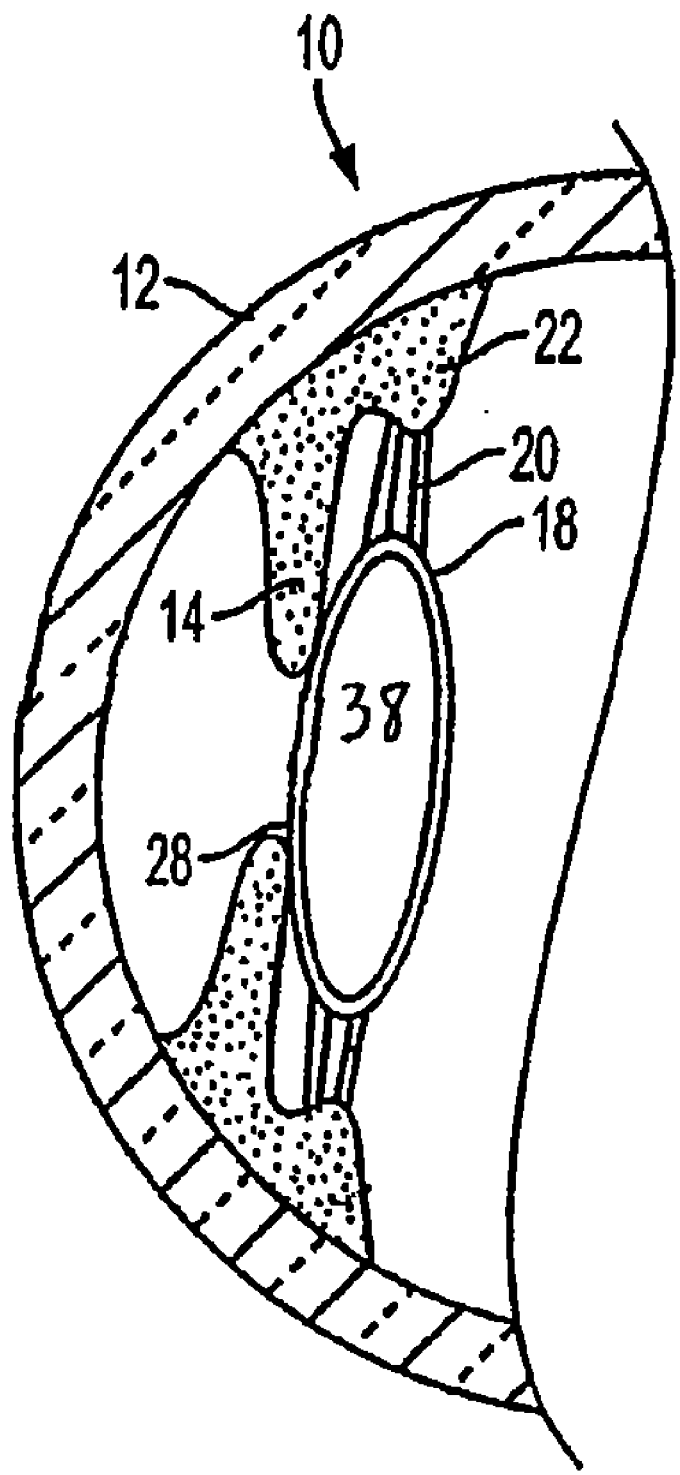
FIG. 4 is a side elevational view in section of the eye shown in FIG. 3 showing placement of a replacement lens into the capsular bag.
Figure 5:
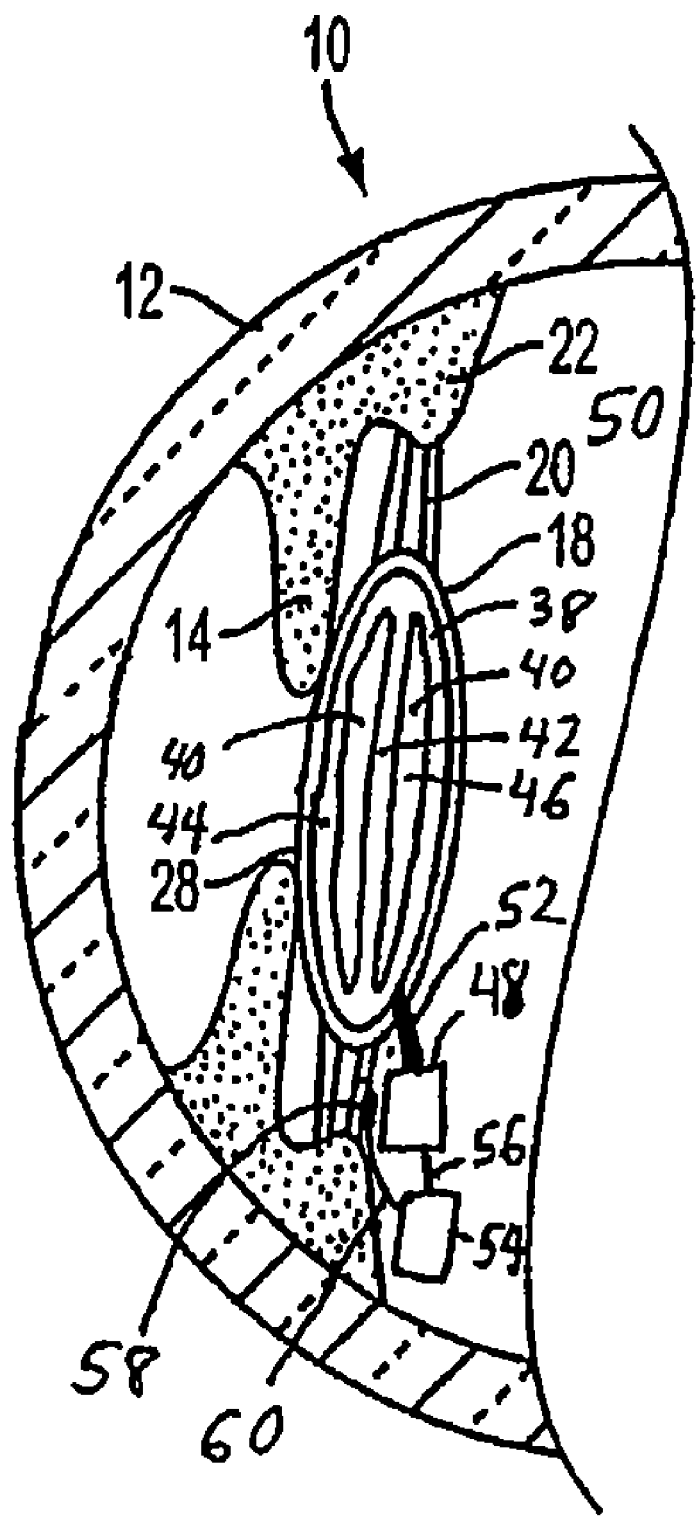
FIG. 5 is a side elevational view in section of the eye shown in FIG. 3 in which a replacement lens is positioned in the capsular bag and a fluidic system and remote power unit are positioned in the posterior chamber.

As shown in FIG. 4, a replacement lens 38 is then positioned within the capsular bag 18. Preferably, the lens 38 can be folded or rolled and inserted through the incision in the capsular bag 18; however, the lens 38 can be rigid and/or can be inserted through a larger second incision in the capsular bag 18 or the initial incision, possibly after the initial incision is widened, or in any other suitable manner. Preferably the lens 38 varies its focal length in response to changes in fluidic pressure within the lens made in accordance with electrical signals; however the lens 38 can change its index of refraction or alter its focal length in any other suitable manner. Since the capsular bag 18 is still in place, the capsular bag can still assist in accommodation; however, it is not necessary for capsular bag 18 to assist with accommodation. The lens, as shown in FIG. 5, preferably includes two chambers 40 set on opposite sides of a substrate 42 and covered with a flexible membrane 44; however, the lens can have one or any other suitable number of chambers. Preferably, the two chambers 40 contain a fluid 46, and preferably the fluid 46 is a sodium chromate solution; however, if desired, one or more of the chambers can contain something other than a fluid or the chambers can contain different fluids or different sodium chromate solutions. The substrate 42 is preferably glass; however, the substrate 42 can be any suitable material. Preferably, the flexible membrane 44 is a biocompatible material; however, the flexible membrane can be any suitable material.

Preferably, the fluidic pressure within the chambers 40 can be altered using a fluidic system 48 which includes a miniature fluidic pressure generator (e.g., a pump or any other suitable device), a fluid flow control device (e.g., a valve or any other suitable device), a control circuit and a pressure sensor; however, the fluidic pressure can be altered in any suitable manner. Further, if desired, a fluidic system 48 does not need a pressure sensor. When subjected to electrical signal, the electronic control circuit of the fluidic system 48 controls the valves and pumps to adjust the fluidic pressure in one or more of the chambers 40. Preferably, the fluidic pressure is adjusted by pumping fluid in or releasing a valve to allow fluid to flow out and back into the system 48; however, the fluidic pressure can be adjusted by pumping fluid out or in any other suitable manner. As a result, the shape and the focal length of the lens 38 is altered, providing accommodation. Lenses that similarly change focal length in response to fluidic pressure changes made in accordance with electrical signals are described in greater detail in "Integrated Fluidic Adaptive Zoom Lens", *Optics Letters*, Vol. 29, Issue 24, 2855-2857, December 2004, the entire contents of which is hereby incorporated by reference.

As shown in FIG. 5, fluidic system 48 is preferably positioned in the posterior chamber 50; however, the fluidic system 48 can be positioned outside the eye, within the sclera, between the sclera and the choroids or any other suitable location. Further, the fluidic system 48 is preferably positioned such that it is not in the visual pathway. A tube 52 fluidly connects the lens 38 and the fluidic system 48. Preferably, the tube 52 passes through a small incision in the capsular bag 18 near the connection of the zonules 20 and the capsular bag 18; however, the tube 52 can pass through the capsular bag in any suitable location.

Preferably, fluidic system 48 includes a power source which is preferably rechargeable through induction or other suitable means such as generating and storing electrical energy using eye and/or head movement to provide the energy to drive the generator; however, fluidic system 48 can be connected to a remote power source 54 as shown in FIG. 5 or to any other suitable power source. Preferably, the remote power source 54 is located in the posterior chamber 50; however, the remote power source 54 can be positioned outside the eye (e.g., under the scalp, within a sinus cavity, under the cheek, in the torso or in any other suitable location), within the sclera, between the sclera and the choroids or any other suitable location. Further, the remote power source 54 is preferably positioned such that it is not in the visual pathway. The remote power source 54 is preferably electrically coupled to the fluidic system 48 by electrically conductive line 56; however, the remote power source 54 can be coupled to the fluidic system 48 in any suitable manner. Further, the remote power source 54 preferably includes a signal generator which can supply control signals to the fluidic system 48 via electrically conductive line 56; however, the remote power source 54 can be without a signal generator, if desired, or can supply control signals to the fluidic system 48 in any suitable manner. Similar remote power sources are described in more detail in U.S. Pat. No. 6,947,782 to Schulman et al., which is herein incorporated by reference in its entirety.

Preferably, the remote power source 54 is coupled to a sensor 58 by electrically conductive line 60; however, the remote power source 54 can be coupled to sensor 58 in any suitable manner. The sensor 58 is preferably a tension sensor positioned on the zonules 20 so that the sensor 58 detects the amount of tension present in the zonules 20; however, the sensor 58 can be a wireless signal sensor, a neurotransmitter sensor, a chemical sensor, a pressure sensor or any other suitable sensor type and/or can be positioned in or near the ciliary muscle 22, at or near the nerve controlling the ciliary muscle 22, in the capsular bag 18 or in any other suitable location. Preferably, the sensor 58 detects the eye's attempt to cause its lens to accommodate; however, the sensor 58 can detect a manual attempt to accommodate the lens 38 (e.g., input through a wireless controller) or any other suitable input. The information detected at the sensor 58 is relayed to the remote power source 54 via line 60, and the signal generator of the remote power source 54 generates a signal in accordance with the information. The signal is sent to the fluidic system 48, which adjusts the fluidic pressure in one or more of the chambers 40 accordingly. Thus, the eye's natural attempts to focus will result in accommodation of lens 38. Response of lens 38 may vary from that of the natural lens; however, the neural systems which control the ciliary muscle 22 (and therefore the tension on the zonules 20), are provided with feedback from the optic nerve and visual neural pathways. As a result, the neural system can learn and adjust to the characteristics of the lens 38.

Figure 6:
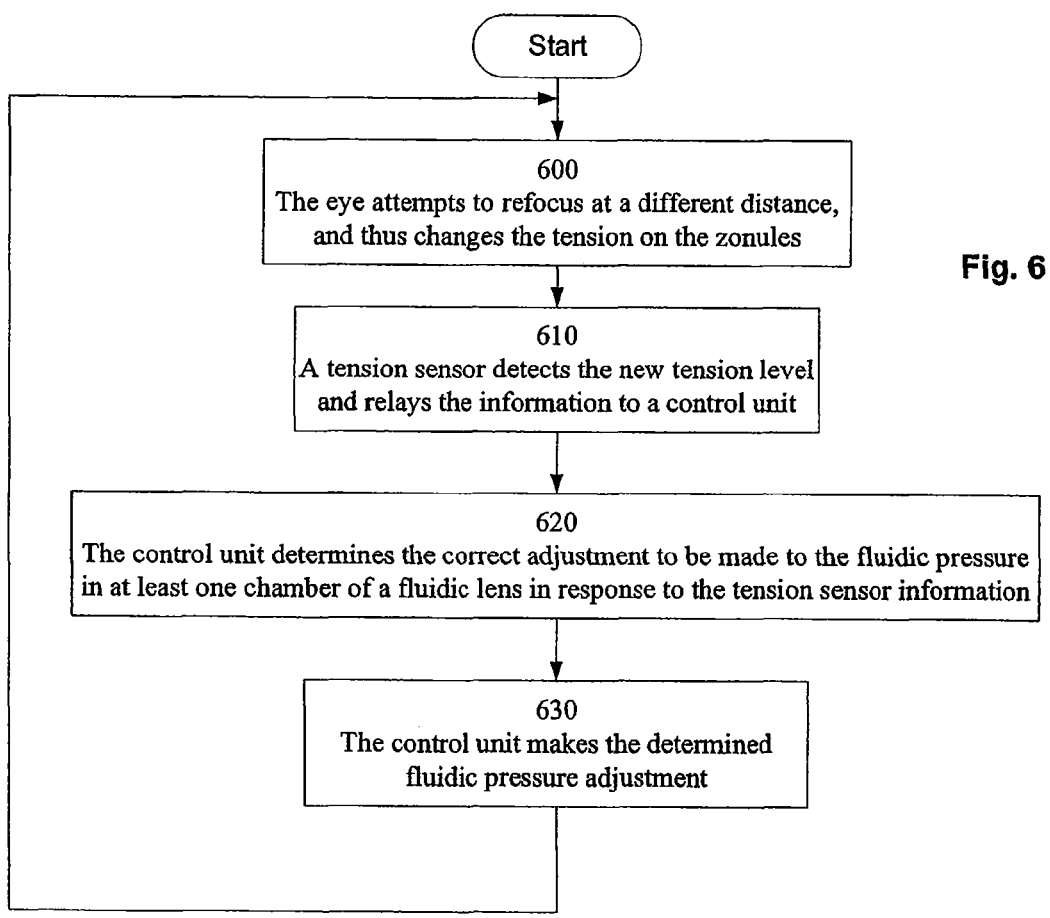
FIG. 6 is a flow chart of the process of accommodation in accordance with one embodiment of the present invention.

The process of accommodation in accordance with one embodiment is shown in FIG. 6. At step 600, the eye attempts to refocus at a different distance, and thus changes the tension on the zonules. At step 610, a tension sensor detects the new tension level and relays the information to a control unit. The control unit preferably includes a remote power source and a fluidic system; however, the control unit can include any suitable devices. At step 620, the control unit determines the correct adjustment to be made to the fluidic pressure in at least one chamber of a fluidic lens in response to the tension sensor information. At step 630, the control unit makes the determined fluidic pressure adjustment and the process repeats at step 600.

Figure 7:
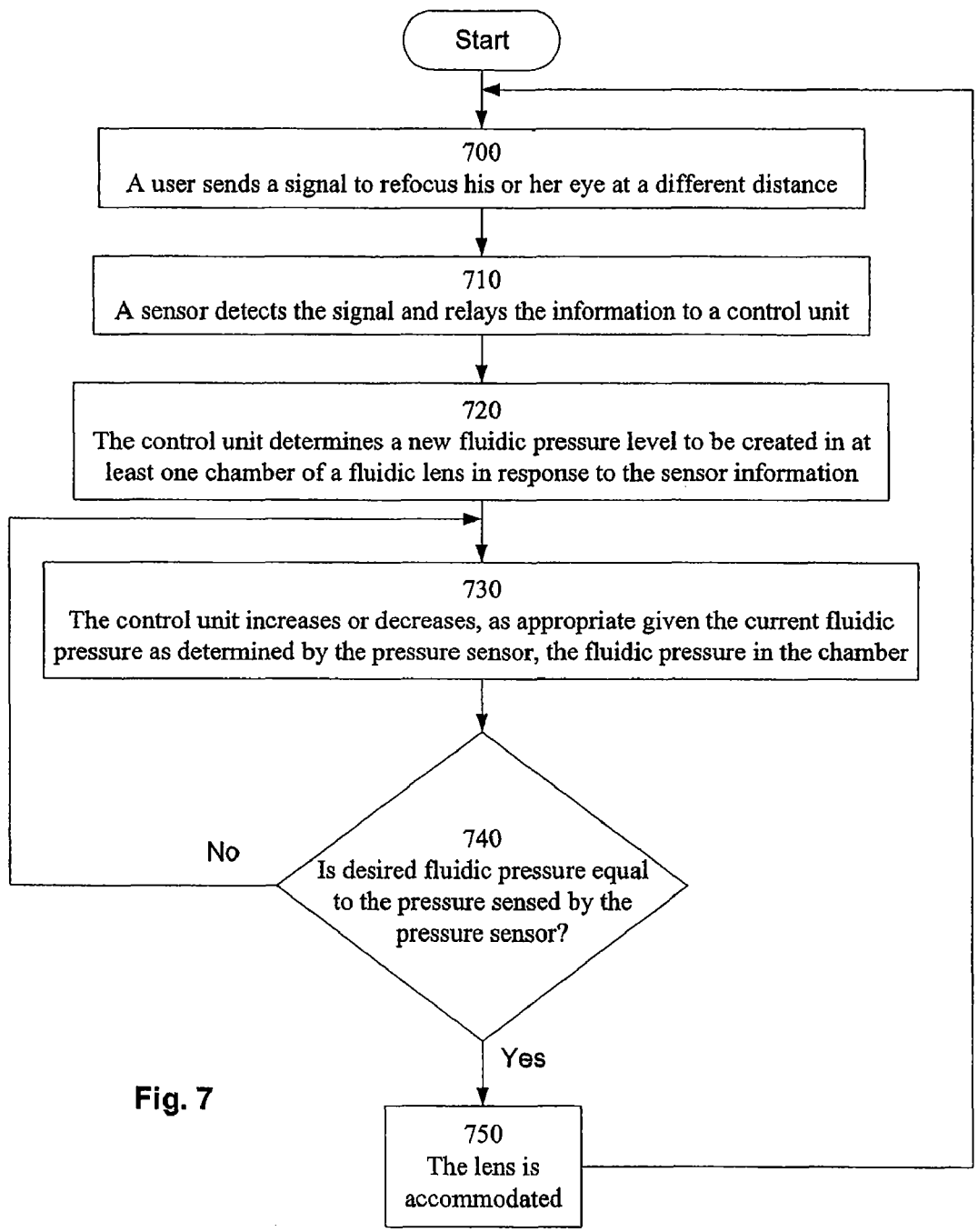
FIG. 7 is a flow chart of the process of accommodation in which the fluidic system includes a pressure sensor for sensing the pressure in at least one of the chambers in accordance with one embodiment of the present invention.

Another process of accommodation in accordance with another embodiment in which the fluidic system includes a pressure sensor for sensing the pressure in at least one of the chambers is shown in FIG. 7. At step 700, a user sends a signal to refocus his or her eye at a different distance. Preferably, the signal is sent wirelessly; however, the signal can be sent in any suitable manner. Further, the signal preferably includes information corresponding to the desired different distance; however, the signal can include information indicating only that the desired distance is closer or farther or any other suitable information. At step 710, a sensor detects the signal and relays the information to a control unit. The control unit preferably includes a remote power source and a fluidic system; however, the control unit can include any suitable devices. At step 720, the control unit determines a new fluidic pressure level to be created in at least one chamber of a fluidic lens in response to the sensor information. At step 730, the control unit increases or decreases, as appropriate given the current fluidic pressure as determined by the pressure sensor, the fluidic pressure in the chamber. At step 740 it is determined whether the desired fluidic pressure is equal to the pressure sensed by the pressure sensor. If the desired fluidic pressure is equal to the pressure sensed by the pressure sensor, at step 750, the lens is accommodated and the process repeats at step 700. If the desired fluidic pressure is not equal to the pressure sensed by the pressure sensor, the process repeats at step 730.

Figure 8:
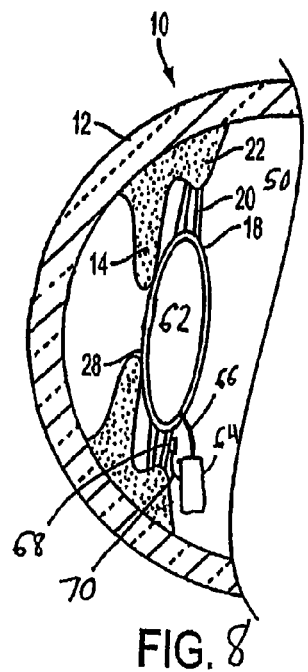
FIG. 8 is a side elevational view in section of the eye shown in FIG. 3 in which a replacement lens is positioned in the capsular bag and a power unit is positioned in the posterior chamber.

FIG. 8 illustrates an alternative accommodating lens 62. Lens 62 responds to electrical stimulation by changing its focal length. Similar to lens 38, lens 62 is preferably placed within the capsular bag 18; however, the lens 62 can be placed in the posterior chamber 50, in place of the capsular bag 18, within the cornea 12, on the surface of the eye or in any other suitable location. Further, it should be noted that any suitable section of the capsular bag can be removed, including but not limited to an anterior portion or a posterior portion around the main optical axis of the eye. If the lens 62 is placed within the capsular bag 18, the capsular bag can assist with accommodation; however, it is not necessary for the capsular bag 18 to assist with accommodation. Lens 62 may have one or more chambers that are at least partly filled with a fluid or other substance; however, lens 62 is not required to have a chamber.

Preferably, lens 62 is a fluid lens that alters its focal length by changing its shape; however lens 62 can be any suitable type of lens and can change its focal length in any suitable manner. The lens 62 preferably includes two immiscible (i.e., non-mixing) fluids of different refractive index (or other suitable optical property); however, the lens 62 is not required to include two immiscible fluids of different refractive index. Preferably, one of the immiscible fluids is an electrically conducting aqueous solution and the other an electrically non-conducting oil, contained in a short tube with transparent end caps; however, the immiscible fluids can be any suitable fluids and can be contained in any suitable container. The internal surfaces of the tube wall and one of its end caps are preferably coated with a hydrophobic coating that causes the aqueous solution to form itself into a hemispherical mass at the opposite end of the tube, where it acts as a spherically curved lens; however, the hydrophobic coating is not required and, if present, can be arranged in any suitable manner. Further, the coating can include any suitable material, including hydrophilic substances.

Preferably, the shape of the lens 62 can be adjusted by applying an electric field across the hydrophobic coating such that it becomes less hydrophobic (a process called "electrowetting" that results from an electrically induced change in surface-tension); however, the shape of the lens 62 can be adjusted by applying an electric field across any suitable portion of the lens 62. Preferably, as a result of this change in surface-tension, the aqueous solution begins to wet the sidewalls of the tube, altering the radius of curvature of the meniscus between the two fluids and hence the focal length of the lens. Increasing the applied electric field can preferably cause the surface of the initially convex lens to become less convex, substantially flat or concave; however increasing the applied electric field can cause the surface of the lens to change in any suitable manner. Preferably, decreasing the applied electric field has the opposite effect, enabling the lens 62 to transition smoothly from being convergent to divergent, or vice versa, and back again repeatably.

The lens 62 can measure 3 mm in diameter by 2.2 mm in length; however the lens 62 can have any suitable dimensions. The focal range of the lens 62 can be any suitable range and can extend to infinity. Further, switching over the full focal range can occur in less than 10 ms or any other suitable amount of time. Preferably, lens 62 is controlled by a DC voltage and presents a capacitive load; however, the lens 62 can be controlled by any suitable voltage and operate with any suitable electrical properties.

Lens 62 is electrically coupled to a power source 64 by electrically conductive line 66; however, lens 62 can be coupled to power source 64 in any suitable manner. Preferably, power source 64 is rechargeable through induction or other suitable means such as generating and storing electrical energy using eye and/or head movement to provide the energy to drive the generator; however, the power source 64 can be non-rechargeable, if desired. Similar to remote power source 54, the power source 64 is preferably located in the posterior chamber 50; however, the power source 64 can be positioned outside the eye (e.g., under the scalp, within a sinus cavity, under the cheek, in the torso or in any other suitable location), within the sclera, between the sclera and the choroids or any other suitable location. Further, the power source 64 is preferably positioned such that it is not in the visual pathway. The power source 64 preferably includes a signal generator which can supply current to the lens 62 via electrically conductive line 66; however, the power source 64 can be without a signal generator, if desired, or can supply control signals to the lens 62 in any suitable manner.

Preferably, the power source 64 is coupled to a sensor 68 by electrically conductive line 70; however, the power source 64 can be coupled to sensor 68 in any suitable manner. The sensor 68 is preferably a tension sensor positioned on the zonules 20 so that the sensor 68 detects the amount of tension present in the zonules 20; however, the sensor 68 can be a wireless signal sensor, a neurotransmitter sensor, a chemical sensor, a pressure sensor or any other suitable sensor type and/or can be positioned in or near the ciliary muscle 22, at or near the nerve controlling the ciliary muscle 22, in the capsular bag 18 or in any other suitable location. Preferably, the sensor 68 detects the eye's attempt to cause its lens to accommodate; however, the sensor 68 can detect a manual attempt to accommodate the lens 62 (e.g., input through a wireless controller) or any other suitable input. The information detected at the sensor 68 is relayed to the power source 64 via line 70, and the signal generator of the power source 64 generates a signal in accordance with the information. The signal is sent and passed through the lens 62, which preferably changes shape as a result of the electrical current flowing through it; however, the lens 62 could change its index of refraction in response to the electrical current flowing through it or change its focal length in any other suitable manner. Preferably, line 70 includes two separate electrical pathways that electrically couple to lens 62 at different, preferably substantially opposite, locations so that one of the pathways can serve as a ground wire; however, the lens 62 can be grounded in any other suitable manner to enable current supplied via line 70 to flow through the lens 62. As a result, similar to lens 38, the eye's natural attempts to focus will result in accommodation of lens 62. Response of lens 62 may vary from that of the natural lens; however, as with lens 38, the neural systems which control the ciliary muscle 22 (and therefore the tension on the zonules 20), are provided with feedback from the optic nerve and visual neural pathways. As a result, the neural system can learn and adjust to the characteristics of the lens 62.

Figure 9:
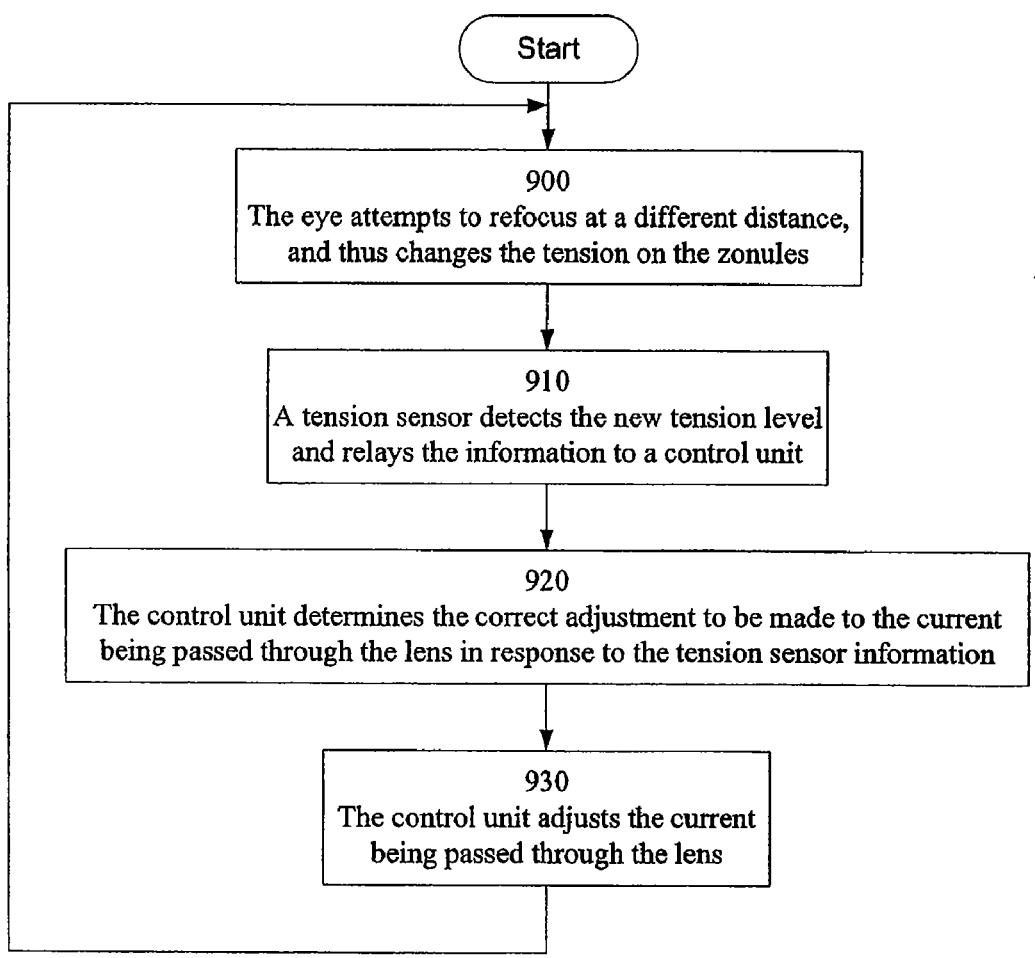
FIG. 9 is a flow chart of the process of accommodation in response to electrical signals in accordance with one embodiment of the present invention.

The process of accommodation in response to electrical signals in accordance with one embodiment is shown in FIG. 9. At step 900, the eye attempts to refocus at a different distance, and thus changes the tension on the zonules. At step 910, a tension sensor detects the new tension level and relays the information to a control unit. The control unit preferably includes a power source; however, the control unit can include any suitable devices. At step 920, the control unit determines the correct adjustment to be made to the current being passed through the lens in response to the tension sensor information. At step 930, the control unit adjusts the current being passed through the lens and the process repeats at step 900.

Figure 10:
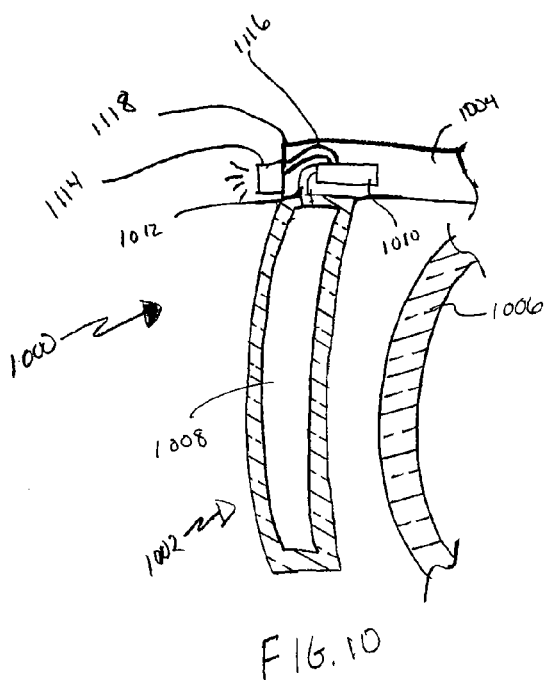
FIG. 10 is a side view in section of another embodiment of the present invention, showing the adjustable lens positioned relative to the eye.
Figure 11:
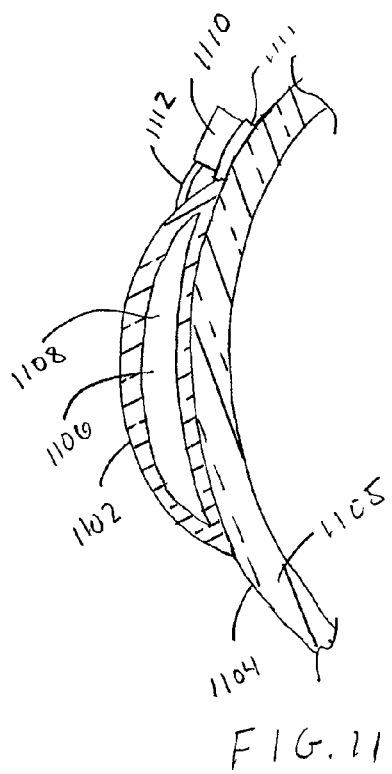
FIG. 11 is a side view in section of another embodiment of the present invention, showing the adjustable lens as a contact lens.

In another embodiment, as illustrated in FIGS. 10-11, the present invention can be used in an external lens. For example, the lens can be configured to be used with spectacles (FIG. 10) or as a contact lens (FIG. 11). The embodiments of FIGS. 10-11 are configured to correct refractive errors in the eye. For example, the present embodiments can correct at least myopia (i.e., be a negative diopter lens), hyperopia and astigmatism. Furthermore, since these embodiments (as discussed in more detail below) can have their refractive properties altered, they are multi-focal lenses. Thus, these lenses can correct, among other disorders, presbyopia, or any combination of disorders.

When configured to be used in conjunction with spectacles 1000, lens 1002 is preferably coupled to a frame 1004 that positions the lens 1002 relative to the cornea 1006 of the eye in any suitable manner. As with previous embodiments, the lens 1002 has a chamber or area 1008 (or multiple chambers or areas, if desired) that is configured to hold a fluid or a mixture of fluids or any other suitable substance. Chamber 1008 preferably includes two immiscible (i.e., non-mixing) fluids of different refractive index (or other suitable optical property); however, the chamber 1008 is not required to include two immiscible fluids of different refractive index. Preferably, one of the immiscible fluids is an electrically conducting aqueous solution and the other an electrically non-conducting oil, contained in a short tube with transparent end caps, as described above; however, the immiscible fluids can be any suitable fluids and can be contained in any suitable container. The above description of the fluids is applicable to the present invention.

Preferably, as with the embodiments above, the shape of the lens 1002 can be adjusted by applying an electric field across the hydrophobic coating such that it becomes less hydrophobic (a process called "electrowetting" that results from an electrically induced change in surface-tension); however, the shape of the lens 1002 can be adjusted by applying an electric field across any suitable portion of the lens 1002. Preferably, as a result of this change in surface-tension, the aqueous solution begins to wet the sidewalls of the tube, altering the radius of curvature of the meniscus between the two fluids and hence the focal length of the lens. Increasing the applied electric field can preferably cause the surface of the initially convex lens to become less convex, substantially flat or concave; however increasing the applied electric field can cause the surface of the lens to change in any suitable manner. Preferably, decreasing the applied electric field has the opposite effect, enabling the lens 1002 to transition smoothly from being convergent to divergent, or vice versa, and back again repeatably. Thus, allowing the lens 1002 to repeatably focus on near and/or far objects.

The focal range of the lens 1002 can be any suitable range and can extend to infinity. Further, switching over the full focal range can occur in less than 10 ms or any other suitable amount of time. Preferably, lens 1002 is controlled by a DC voltage and presents a capacitive load; however, the lens 1002 can be controlled by any suitable voltage and operate with any suitable electrical properties.

Lens 1002 is electrically coupled to a power source 1010 by electrically conductive line 1012; however, lens 1002 can be coupled to power source 1010 in any suitable manner. Preferably, power source 1010 is rechargeable through direct electrical current, induction or other suitable means such as generating and storing electrical energy using eye and/or head movement to provide the energy to drive the generator; however, the power source 1010 can be non-rechargeable, if desired. Power source 1010 is preferably located on the frame 1004 of spectacles 1000; however, the power source 1010 can be positioned in any suitable location. The power source 1010 preferably includes a signal generator which can supply current to the lens 1002 via electrically conductive line 1112; however, the power source 1010 can be without a signal generator, if desired, or can supply control signals to the lens 1002 in any suitable manner.

Preferably, the power source 1010 is coupled to a sensor 1114 by electrically conductive line 1116; however, the power source 1010 can be coupled to sensor 1116 in any suitable manner (e.g. wirelessly). The sensor 1114 is preferably a distance sensor positioned on the front 1118 of frame 1004 so that the sensor 1114 detects the distance of an object away from the eye (such as a laser range finder); however, the sensor 1114 can be any suitable sensor type. Preferably, the sensor 1114 is positioned relative to the eye such that it detects the distance a specific object is from the eye and adjusts the lens 1002 accordingly; however, the sensor 1114 can detect a manual attempt to adjust the lens 1002 (e.g., input through a wireless controller or direct push buttons) or any other suitable input. The information detected at the sensor 1114 is relayed to the power source 1010 via line 1116, and the signal generator of the power source 1010 generates a signal in accordance with the information. The signal is sent and passed through the lens 1002, which preferably changes shape as a result of the electrical current flowing through it; however, the lens 1002 could change its index of refraction in response to the electrical current flowing through it or change its focal length in any other suitable manner. Preferably, line 1116 includes two separate electrical pathways that electrically couple to lens 1102 at different, preferably substantially opposite, locations so that one of the pathways can serve as a ground wire; however, the lens 1002 can be grounded in any other suitable manner to enable current supplied via line 1116 to flow through the lens 1002.

Additionally, the lens 1002 can be wirelessly coupled to a sensor, such as sensor 64, described above and adjust based on signals from the cilliary muscles and/or the zonules. Response of lens 1002 may vary from that of the natural lens; however, as with lenses described above, the neural systems which control the ciliary muscle 22 (and therefore the tension on the zonules 20), are provided with feedback from the optic nerve and visual neural pathways. As a result, the neural system can learn and adjust to the characteristics of the lens 1002.

FIG. 11 illustrates another embodiment of the present invention, where the lens 1102 is a contact lens that is positioned on the external surface 1104 of the cornea 1105.

As with lens 1002, lens 1102 includes a chamber or area 1106 (or multiple chambers or areas, if desired) having a fluid 1108 therein. Prefereably, fluid 1108 is the same as the fluid described above for lens 1002 and operates in the substantially the same manner; however, any suitable fluid and/or substance or combination thereof can be used.

As described above, lens 1102 is coupled to a power source 1110 via an electrical wire 1112, or by any other suitable means. The power source 1110 is coupled to lens 1102 in any suitable manner (e.g., attached to a protrusion 1111). Power source 1110 and electrical wire 1112 are configured and operate in substantially the same manner as described above for lens 1002. Any description of lens 1002 and power source 1010 is applicable to lens 1102 and power source 1110.

Furthermore, lens 1102 can have a distance sensor (or any other sensor) that is located outside the eye and wirelessly coupled or directly wired to power source 1110, as described above. The sensor can be a sensor coupled to the lens 1102 (or any other suitable place on or adjacent the eye) or it can be located in the eye, and operate in substantially the same manner as sensors described above.

Additionally, both lens 1002 and 1102 can have their respective refractive properties altered in any manner described herein and are not limited the specific descriptions above. For example, lens 1102 and lens 1002 can have their respective refractive properties altered by changing the fluidic pressure as described above.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A lens system comprising:
   a lens having at least one chamber housing a substance, said lens having a rigid wall and being configured to be positioned externally and relative to an eye;
   a control unit operable to control the exterior shape and focal length of said lens by adding fluid to or removing fluid from the chamber to change the pressure of the substance in the chamber so as to control of the shape and focal length of said lens to alter light rays passing through said lens, and focus the light rays on the retina of the eye; and
   wherein the chamber is at least partially enclosed by a flexible membrane, such that the lens is capable of having the shape and focal length altered so as to be a negative diopter lens.

2. The lens system of claim 1, wherein the control unit is operable to receive a signal from a sensor, wherein when the signal is received, the signal includes information about a condition.

3. The lens system of claim 2, wherein the condition is the distance an object is from the lens.

4. The lens system of claim 2, wherein the sensor is an integral part of the lens system and is configured to send automatic updates to the control unit such that the shape of the lens is continuously altered.

5. The lens system of claim 1, wherein said lens is a contact lens.

6. The lens system of claim 1, wherein said lens is configured for use in spectacles.

7. The lens of claim 1, wherein the control unit is operable to control the shape and focal length of said lens by increasing the pressure of the substance in the chamber.

8. The lens of claim 1, wherein the control unit is operable to control the shape and focal length of said lens by decreasing the pressure of the substance in the chamber.

9. The lens system of claim 1, wherein the chamber is enclosed by at least two flexible members disposed opposite each other, such the lens is capable of having the shape and focal length altered so as to be a negative diopter lens.

10. The lens system of claim 1, wherein the control unit is operable to receive manual input signals to control the exterior shape and focal length of the lens.

11. The lens system of claim 1, wherein the at least one chamber includes two chambers.

12. A lens system comprising:
    a lens configured to be positioned external to the eye and including a flexible membrane and a rigid wall, the flexible membrane at least partially defining an exterior surface and that defines at least one interior chamber;
    a fluid contained within the chamber;
    a control unit configured to change the fluidic pressure in the chamber by adding fluid to or removing fluid from the chamber, so that the shape of the exterior surface of the lens is altered;

wherein the chamber is at least partially enclosed by a flexible membrane, such the lens is capable of having the shape and focal length altered so as to be a negative diopter lens.

13. The lens system of claim 12, wherein the control unit is configured to increase the fluidic pressure in the chamber, so that the shape of the lens is altered.

14. The lens system of claim 12, wherein the control unit is configured to decrease the fluidic pressure in the chamber, so that the shape of the lens is altered.

15. The lens system of claim 12, wherein said lens is configured to be positioned at a location selected from the group consisting of on the external surface of the cornea and adjacent but spaced from the cornea.

16. The lens system of claim 12, further comprising: a sensor, wherein said sensor is configured to sense a condition and said control unit is operable to receive a signal from said sensor, and wherein when the condition is sensed and the signal is received, the signal includes information about the condition.

17. The lens system of claim 16, wherein said condition is the distance an object is from the lens.

18. The lens system of claim 17, wherein said distance is determined using a laser range finder.

19. The lens system of claim 16, wherein the condition is the distance of the object from the eye.

20. The lens system of claim 12, wherein said lens is configured for use in spectacles.

21. The lens system of claim 12, wherein the at least one interior chamber includes two interior chambers.

22. The lens system of claim 12, further comprising a sensor that is an integral part of the lens system and is configured to send automatic updates to the control unit such that the shape of the lens is continuously altered.

* * * * *